United States Patent [19]
Lin et al.

[11] Patent Number: 6,042,714
[45] Date of Patent: Mar. 28, 2000

[54] METHOD AND CHEMICAL SENSOR FOR DETERMINING CONCENTRATIONS OF HYDROGEN PEROXIDE AND ITS PRECURSOR IN A LIQUID

[75] Inventors: Meng Shan Lin, Taipei Hsien; Yi Cong Wu, Taichung Hsien; Jung Sheng Lai, Ping Tung Hsien; Bor Iuan Jan, Ping Tung City; Ta Feng Tseng, Kao Hsiung Hsien; Wei Chung Shih, Taipei, all of Taiwan

[73] Assignee: National Science Council, Taipei, Taiwan

[21] Appl. No.: 08/984,775

[22] Filed: Dec. 4, 1997

[30] Foreign Application Priority Data

May 2, 1997 [TW] Taiwan ................................. 86105885

[51] Int. Cl.[7] .................................................. G01N 27/26
[52] U.S. Cl. ...................... 205/782; 205/777.5; 204/403; 204/416; 204/419
[58] Field of Search ..................................... 204/416, 403, 204/419; 205/777.5, 782, 783, 786, 794.5

[56] References Cited

U.S. PATENT DOCUMENTS

| | | |
|---|---|---|
| 4,340,448 | 7/1982 | Schiller et al. . |
| 4,545,382 | 10/1985 | Higgins et al. ......................... 128/635 |
| 4,713,165 | 12/1987 | Conover et al. . |

FOREIGN PATENT DOCUMENTS

| | | |
|---|---|---|
| 9521934A1 | 2/1995 | WIPO . |

OTHER PUBLICATIONS

Chen–Xin et al. Catalytic oxidation of reduced nicotinamide dinucleotide at a microband gold electrode modified with nickel hexacyanoferrate. Analytica Chimica Acta, vol:310, Iss. 1, Jun. 1995.

Milardovic et al. Glucose determination in blood samples using flow injection analysis and an amperometric biosensor based on glucose oxidase immobilized on hexacyanoferrate modified nickel electrode. Analytica Chimica Acta, vol:350, Iss. 1–2, Sep. 1997.

Chen–Xin et al. Cobalt Hexacyanoferrate modified microband gold electrode and its electrocatalytic activity for oxidation of NADH. Journal of Electroanalytical Chemistry, vol:397, Iss. 1–2, Nov. 1995.

*Primary Examiner*—Robert J. Warden, Sr.
*Assistant Examiner*—Jennifer McNeil
*Attorney, Agent, or Firm*—Fish & Richardson P.C.

[57] ABSTRACT

A new method which employs a mixed-valence cluster of $M_y^{z+}[Fe(II)(CN)_6]$ coated on an electrode surface to determine hydrogen peroxide concentration electrochemically is developed. M of the mixed-valence compound can be Co, Ni, Cr, Sc, V, Cu, Mn, Ag, Eu, Cd, Zn, Ru or Rh; z is the valence state of M; and y=4/z. In addition, this invention also reveals a new approach to determine a concentration of a hydrogen peroxide precursor, wherein a catalyst is immobilized in the matrix or on the surface of the mixed-valence compound on the electrode. In a typical biochemical system, the catalyst can be a glucose oxidase and blood sugar is catalyzed to form hydrogen peroxide.

26 Claims, 4 Drawing Sheets

METHOD AND CHEMICAL SENSOR FOR DETERMINING CONCENTRATIONS OF HYDROGEN PEROXIDE AND ITS PRECURSOR IN A LIQUID

FIELD OF THE INVENTION

This invention is related to a new electrochemical method of determining hydrogen peroxide concentration. This new method also can be applied to determine the concentration of a hydrogen peroxide precursor which results in the formation of hydrogen peroxide in the presence a catalyst.

BACKGROUND

Measurement of hydrogen peroxide is very crucial in both biomedical and environmental systems. Industries such as plastic and food processing also require hydrogen peroxide. In many biological reaction systems, hydrogen peroxide is a resultant product of several biologically important oxidases. Therefore, it is an important indicator to monitor various biological reactions. Various methods of measuring $H_2O_2$ concentration have been developed including fluorometry, fiber-optics, chemiluminescene, and electrochemical methods for aqueous and gaseous samples.

In this invention, an electrode is used as a reactor to generate a desired mixed-valence cluster with proper catalytic property of hydrogen peroxide onto the electrode surface, which serves as a chemical sensor to determine the concentration of $H_2O_2$. A mixed-valence cluster is a polynuclear compound with two or more metal clusters which linked by a ligand [D. V. Brown, Mixed-Valence Compounds, D. Reidel Press, Boston 1980]. A typical mixed-valence compound is prepared by mixing aqueous solutions of the anion and cationic metals, which result in the immediate formation (precipitation) of mixed-valence product. In addition to its catalytic property of hydrogen peroxide, it has been found that the electrons are de-localized on the entire complex and the evidence of detecting various redox potential between the two metal centers proves the existence of electronic interactions in the complex. This characteristic of a possible inter-valence charge transfer (IVCT) through the bridging ligand of the complexes can be used as electronic wire [M. D. Ward, Chemical Society Reviews, 1995, 24, 121]. Based on these findings, the electron transfer direction is propagated directionally through bridging ligands at the control of electrode.

Due to a relative high overvoltage requirement and possible interference, a direct amperometric detection scheme for $H_2O_2$ seems not feasible for environmental and biological samples. Few years ago an attempt [M. S. Lin, et al., Electroanalysis 1990, 2, 511; M. S. Lin, et al., Anal. Chim. Acta 1990, 234,453.] was made to develop a peroxidase containing system so that $H_2O_2$ concentration could be measured, although the sensitivity of the detection is limited. However, the catalyst modified electrode may provide a better solution for this problem. Recently, Wang et al. utilized various carbon materials as transducers that were modified with a series of precious metal such as Pt, Pd, and Rh to reduce the overvoltage for the determination of biological significant through $H_2O_2$ in biological systems [J. Wang, and L. Angnes, Anal. Chem. 1992, 64, 456.; Joseph Wang and Qiang Chen, Anal. Chem. 1994, 66, 1007–1011; Joseph Wang, Jie Liu, Liang Chen, and Fang Lu, Anal.Chem. 1994, 66, 3600; Joseph Wang, Fang Lu, L. Angnes, Jie Liu, H. Sakslund, Q. Chen, M. Pedrero, L. Chen, and O. Hammerich, Anal. Chim. Acta, 1995, 305, 3].

The method of monitoring $H_2O_2$ concentration by amperometry in the absence of catalyst requires a high overvoltage, which in turn makes it easily interfered by other oxidizable compounds such as ascorbic acid, uric acid, dopamine, cystein, and acetaminophen, in biological systems.

In the past thirty years, various glucose chemical sensors have been invented. Most of them were designed to monitor reactants (such as glucose and $O_2$) or products (such as $H_2O_2$) of an enzymatic reaction. Measurement of glucose concentration by directly catalyzing glucose has an in situ advantage which is no enzyme is needed; however, other hydrocarbon compounds in blood as well as glucose are also catalyzed. Consequently, this method suffers the lack of selectivity. In addition, its monitoring potential (0.5 V) would not prevent the interference from the easily oxidizable compounds in blood.

The most common approach in many glucose biosensor systems was designed to monitor $H_2O_2$ concentration, wherein a glucose oxidase was used as an indentifier. By employing an electrode as a transducer in an electrochemical system, an external potential higher than 0.9 V is required to oxidize the $H_2O_2$; thus, this high potential might result in undesirable interference of oxidation current generated from other biochemically active compounds such as ascorbic acid, uric acid, . . . etc.

In the Joseph Wang, et al. 1990's articles mentionedabove, a series of precious metals (such as rhodium, ruthenium, palladium, . . . etc.) were utilized in the $H_2O_2$ monitoring system so that the overvoltage could be reduced. Joseph Wang and Lucio Angnes (1992) electrochemically deposited Rh on a carbon-filament microelectrode surface. Their approach could reduce the $H_2O_2$ monitoring potential from +0.9 V to +0.3 V (vs. Ag/AgCl). The response time of the system for the modified electrode was only 3 seconds. The detection limit was $1 \times 10^{-4}$ M. In 20 repeated runs the relative standard deviation was 2.1%. However, it was also observed that the electrode signal decreased by 18% after 15 days of operation. Moreover, the interference from ascorbic acid, uric acid, . . . etc. was still not overcome.

A similar experiment was conducted by Joseph Wang and Qiang Chen (1994) by electrochemical depositing a glucose oxidase and Rh on a carbon electrode surface. This approach which employed Rh as a catalyst in the measurement of $H_2O_2$ concentration could reduce the monitoring potential from +0.6 V to +0.05 V. This modified electrode could prevent the interference from ascorbic acid, uric acid and the like. This modified carbon electrode could last for 140 days with the same activity.

More recently, Wang et al. in their 1995's article blended rhuthenium into a carbon powder paste and formed a printed carbon electrode, then employed glucose oxidase and phenol on the electrode surface at 0.8 V potential so that polyphenol was formed, and thus glucose oxidase was immobilized on the electrode surface. The $H_2O_2$ monitoring potential of this electrode was +0.4 V, i.e. an oxidation current of $H_2O_2$ was able to be detected at this potential. However, electrochemically active compounds in blood such as ascorbic acid had a 0.05 V ox potential, uric acid at 0.3 V, and acetaminophen was 0.25 V. Therefore, at +0.4 V glucose monitoring potential may cause a great interference. The authors of this article had used this electrode at a fixed potential of 0.2 V to detect glucose, and found that the detect limit (S/N=3) was about $2 \times 10^{-4}$ M, a linear range was upto to 1.5 mM, and the relative standard deviation was 0.9% in 25 repeated runs.

SUMMARY

This invention disclose a new chemical sensor to monitor $H_2O_2$ concentration in a liquid. The $H_2O_2$ chemical sensor includes a transducer which is able to conduct an electric current and a mixed-valence compound deposited on a surface of the transducer. The mixed-valence compound has a formula as follows:

$$M_{y'}^{z+}[Fe(II)(CN)_6]$$

where M can be Co, Ni, Cr, Sc, V, Cu, Mn, Ag, Eu, Cd, Zn, Ru, or Rh; z is the valence of M; and y=4/z. This invention also reveals a chemical sensor to monitor a concentration of a $H_2O_2$ precursor. The $H_2O_2$ precursor is defined as a compound that can produce $H_2O_2$ in said liquid under appropriate reaction conditions. The $H_2O_2$ precursor chemical sensor contains the transducer, and a composition deposited on a surface of the transducer. The composition comprises the mixed-valence compound (I) and can catalyze the reaction.

Preferably, in the mixed-valence compound of formula (I), M is Co, z=2 and y=2.

Preferably, in the mixed-valence compound of formula (I), M is Cr, z=2 and y=2.

Preferably, in the mixed-valence compound of formula (I), M is Ni, z=2 and y=2.

Preferably, the $H_2O_2$ precursor is glucose, urea or cholesterol, and the catalyst is glucose oxidase, urea oxidase, or cholesterol oxidase. This invention also discloses a new method to measure $H_2O_2$ concentration electrochemically. The method includes the following steps:

a). Immersing a counter electrode, a reference electrode and the $H_2O_2$ chemical sensor of the present invention as a working electrode into a solution under reaction conditions.

b). Obtaining a steady electric current from the working electrode by conducting an apmerometry analysis, where a fixed potential ranging from +0.1 V to −0.2 V between the working electrode and the reference electrode is maintained, when the reference electrode is 3 M KCl Ag/AgCl electrode.

c). Comparing the steady electric current from b) with steady electric currents obtained from solutions having known $H_2O_2$ concentrations under the same operating conditions and the same fixed potential used in steps a) and b).

The operating conditions includes stirring the solution with a constant stirring speed so that the solution is in a homogeneous phase, and adding a proper pH-buffer to maintain a substantially constant pH. Selectively, an electrolyte is added to the measured solution. The constant pH is preferably between 3 to 7.

The invention further discloses a new method for measuring a concentration of a $H_2O_2$ precursor. The method involves the following steps.

A). Immersing an counter electrode, a reference electrode and the $H_2O_2$ precursor chemical sensor of the present invention as a working electrode into a solution under reaction conditions.

B). Obtaining a steady electric current from the working electrode by conducting an apmerometry analysis, where a fixed potential ranging from +0.1 V to −0.2 V between the working electrode and the reference electrode is maintained, when the reference electrode is 3 M KCl Ag/AgCl electrode.

C). Comparing the steady electric current from B) with steady electric currents obtained from solutions having known $H_2O_2$ precursor concentrations under the same operating conditions and the same fixed potential used in steps A) and B).

The operating conditions includes stirring the solution with a constant stirring speed so that the solution is in a homogeneous phase, and adding a proper pH-buffer to maintain a substantial constant pH. Selectively, an electrolyte is added to the measured solution. The constant pH is preferably between 3 to 7

Preferably, a phosphate buffer solution having a pH of about 6 is used as the pH-buffer, and an alkali metal halide is added to the measured solution as an electrolyte in the methods of the present invention, when M is Co, z=2 and y=2 in the formula (I). In addition to the phosphate buffer, citrate buffer, borate buffer, perchlorate buffer, and acetate buffer also can be used.

When M is Ni, z=2 and y=2 in the formula (I), an acetate buffer having a pH of about 4 is preferably used as the pH-buffer in the methods of the present invention (no electrolyte is added because the buffer serves the same purpose). In addition to the acetate buffer, citrate, borate, and phosphate buffer solutions also can be used.

Preferably, a succinate buffer solution having a pH of about 6 is used as the pH-buffer, and no electrolyte is added to the measured solution (because the succinate buffer serves the same purpose) in the methods of the present invention, when M is Cr, z=2 and y=2 in the formula (I). In addition to succinate buffer, phosphate, acetate, borate, imidazole, citrate, ammonium chloride, and glycine buffers can also be used.

Preferably, in the methods of the present inventions, the fixed potential ranges between 0 and −200 mV.

In this invention, the measured solution is preferably kept at a constant temperature near the room temperature, 15–30° C.

Based on electrochemistry basics, it is possible that the mixed-valence compound (I) in this invention can deposit on the surface of the transducer in the form of an intermediate, i.e., a mixed-valence compound having the following formula:

$$M_{y'}^{z+}[Fe(III)(CN)_6], \text{ where } y'=3/z'.$$

When this intermediate mixed-valence compound is used as a working electrode to measure $H_2O_2$ concentration or $H_2O_2$ precursor concentration, it will be reduced immediately to the mixed-valence compound of formula (I); therefore, it can be used to measure $H_2O_2$ concentration or the concentration of $H_2O_2$ precursor. Thus, the intermediate mixed-valence compound is contemplated as an equivalent in function as the mixed-valence compound of formula (I).

DETAILED DESCRIPTION OF THE INVENTION

Figure 1:
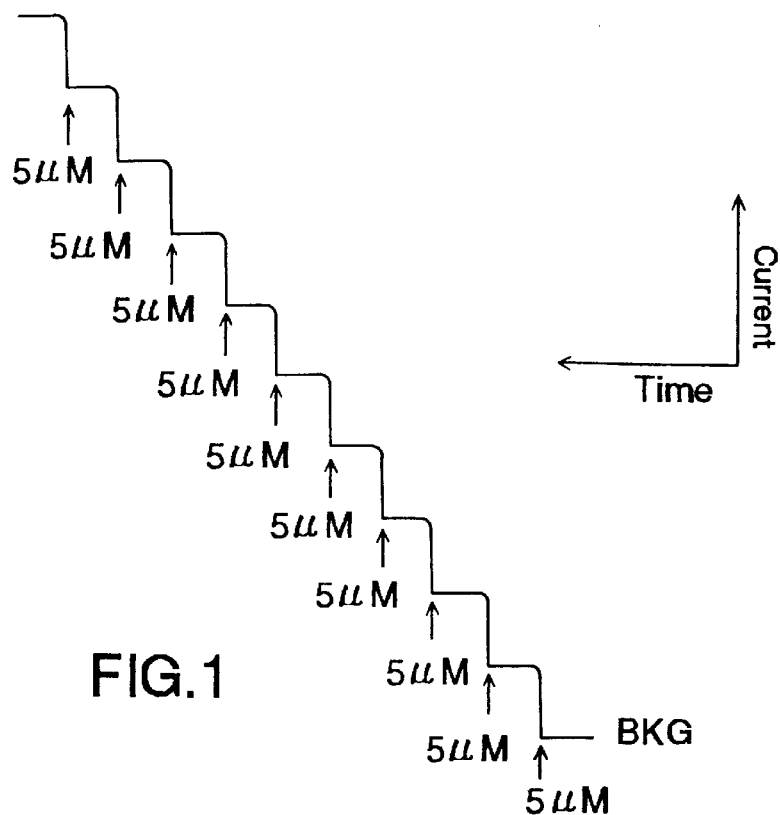
FIG. 1 shows a response of a working electrode upon ten successive injections of 0.05 M $H_2O_2$ solution to provide an increment in $H_2O_2$ concentration of 5 μM for each addition in an amperometry analysis, where the x-axis is time, the y-axis is current (μA), and BKG represents blank background value. The working electrode is a chemical sensor containing $Co_2[Fe(II)(CN)_6]$ prepared according to an embodiment of the present invention.

A new chemical sensor designed to measure $H_2O_2$ concentration is provided in the present invention. The $H_2O_2$ chemical sensor comprises a mixed-valence compound deposited on a surface of a transducer, for example, a electrochemical electrode. The mixed-valence compound has the following formula:

$$M_y^{z+}[Fe(II)(CN)_6] \quad (I)$$

wherein M is Co, Ni, Cr, Sc, V, Cu, Mn, Ag, Eu, Cd, Zn, Ru or Rh; z is the valence state of M; and y=4/z.

The mixed-valence compound (I) provides the chemical sensor with electrode assisted catalysis in an amperometric measurement of $H_2O_2$ concentration in a given solution, wherein the chemical sensor is used as a working electrode. Further, Fe (II) of the mixed-valence compound (I) is oxidized to Fe(III) by $H_2O_2$ in the amperometric measurement of $H_2O_2$, and creates an electronic hole sink therein. The electronic hole is then transferred to the transducer via the inter-valence charge transfer characteristic of the mixed-valence compound (I), so that a current loop is formed. It is apparent that an electrode modified with this mixed-valence compound (I) is also feasible for use in amperometric measurement of oxygen concentration in a given solution provided that the given solution contains no compound having oxidizing ability strong than oxygen.

The $H_2O_2$ chemical sensor of the present invention has a fast response time ($t_{95\%}$), a broad linear range of concentration vs. current, and a high sensitivity, when it is used as a working electrode in an amperometric measurement of $H_2O_2$ concentration in a given solution and when the potential of the chemical sensor is at 0.1 to −0.2 V (vs. 3 M KCl Ag/AgCl reference electrode). In one of the preferred embodiments of the present invention, $t_{95\%}$=6 seconds, the linear range of $H_2O_2$ concentration is from $6.28 \times 10^{-8}$ M to $1.10 \times 10^{-3}$ M (correlation coefficient 0.999), and a sensitivity of 11.8 $\mu A/mM\text{-}mm^2$.

When a catalyst is immobilized in the matrix or on a surface of the mixed-valence compound deposited on the transducer, and the catalyst can catalyze a compound in a given solution to produce $H_2O_2$, it is apparent that this modified transducer is able to be used to determine the compound concentration. The catalyst is called "identifier" and the compound is call "a $H_2O_2$ precursor" in this invention.

By blending the mixed-valence compound with various oxidases (such as glucose oxidase, urea oxidase, and cholesterol oxidase) a series of new biochemical sensors can be prepared and applied to medical, biomedical research, including diagnostic applications. The new biochemical sensors derived from this invention have excellent specificity originated from the specificity of the oxidases. In addition, the transducer modified by the mixed-valence compound is able to monitor the $H_2O_2$ concentration at a potential which will not be interfered by other undesirable biochemical compounds in blood (such as ascorbic acid, uric acid, dopamine, cystein and acetaminophen, etc.). Furthermore, by adding proper electrolyte and pH buffer the interference from oxygen (a strong reducible compound) is also prevented. The mixed-valence compound in this invention has low solubility in water, and thus it can be applied to interfacial chemistry of electrochemical analysis.

The preparation of the $H_2O_2$ chemical sensor of the present invention is simple. For example, CN-ligand-containing iron complexes such as $K_3[Fe(CN)_6]$ and $K_4[Fe(CN)_6]$ and various metal salts such as $Co(NO_3)_2$, $NiCl_2$, and $Cr(NO_3)_3$ are mixed in an aqueous medium to form co-precipitate which is then coated on an electrode. By applying an adequate reduction potential to the electrode in an electroplating or undergoing a cyclic voltammetry, a coating of the mixed-valence compound will be formed on the electrode surface. Alternatively, the $H_2O_2$ chemical sensor of the present invention can be prepared by directly using the resultant aqueous medium as an eletrolyte and undergoing the electroplating or cyclic voltammetry. When an identifier is mixed with the co-precipitate or mixed in the aqueous medium, a coating of the mixed-valence compound containing immobilized identifier will be formed on the electrode surface after the electroplating or the cyclic voltammetry, and thus a $H_2O_2$ precursor chemical sensor of the present invention is prepared.

The invention will be further illustrated by the following examples. The following examples are only meant to illustrate the invention, but not to limit it.

Example 1
$Co_2[Fe(II)(CN)_6]$ Cobalt(II)Hexacyanoferrate Chemical Sensor (1). Pretreatment of Electrode A glassy carbon ring-disk electrode (RDE 0032, Princeton Applied Research, 6 mm outer diameter) was polished using 1 $\mu$m diamond suspension, and sonicated for five minutes in deionized water. The electrode surface was then polished with 0.1 $\mu$m $Al_2O_3$ powder, sonicated for 5 minutes in a deionized water twice followed by rinsing with deionized water twice. Subsequently, the electrode surface was checked by a cyclic voltammetry (BAS 100W, Bioanalytical Systems) to ensure free of contamination.

(2). Preparation of a Glassy Carbon Ring-disk Working Electrode

The pretreated glassy carbon ring-disk electrode, a home-made 3 M KCl Ag/AgCl reference electrode, and a platinum wire counter electrode were immersed into a 0.1 M KCl (pH=3) electroplating solution containing 15 mM $Co(NO_3)_2.6H_2O$ and 15 mM $K_3[Fe(III)(CN)_6]$. The applied potential was maintained at −0.1 V (vs. Ag/AgCl) for 6 hours at 250° C. and 400 rpm to form a thin layer on the glassy carbon ring-disk electrode. The modified glassy carbon ring-disk electrode was then conditioned in a 0.1 M KCl (pH=3) eletrolyte for 30 minutes to obtain a working electrode.

An element analysis of the thin layer deposited on the working electrode was conducted with Heraeus CHN-O Rapid Element Analyzer and the composition was found as $Co_2[Fe(CN)_6]3H_2O$. A FT-IR (FTS-40, Bio-rad) spectrum indicated absorption peaks at 2080 cm.$^{-1}$ (–CN), 457 cm$^{-1}$ (FeCN), and 593 cm$^{-1}$ (FeC).

(3). Measurement Conditions

The working electrode prepared above, a homemade 3 M KCl Ag/AgCl reference electrode, and a platinum wire counter electrode were immersed in a 0.05 M phosphate buffer, pH=6 (Riedel-de Haen, RDH) with 0.05 M KCl solution in an electrochemical cell. A bi-potentiostat (model PAR, 366A, Princeton Applied Research) was used to control the applied voltage at 0 mV (vs. Ag/AgCl). The detection temperature of the electrochemical cell was kept at 25° C. with a circulator (Modle B402, Firstek Scientific). The phosphate buffer in the cell was stirred constantly at 900 rpm with a motor controlled rotor (Model 636, Princeton Applied Research).

0.05M hydrogen peroxide solution was prepared by mixing 172 $\mu$l hydrogen peroxide (35%) with 40 ml of 0.05 M phosphate buffer (pH=6) with 0.05 M KCl solution and the solution was stored in 4° C. This $H_2O_2$ solution was added to the phosphate buffer in the cell at a constant time interval to provide an increment in $H_2O_2$ concentration of 5 $\mu$M so that steady-state amperometric measurements of hydrogen peroxide concentration were conducted. The results of ten successive injections are shown in FIG. 1, wherein x-axis is time, and y-axis is current ($\mu$A).

Figure 2:
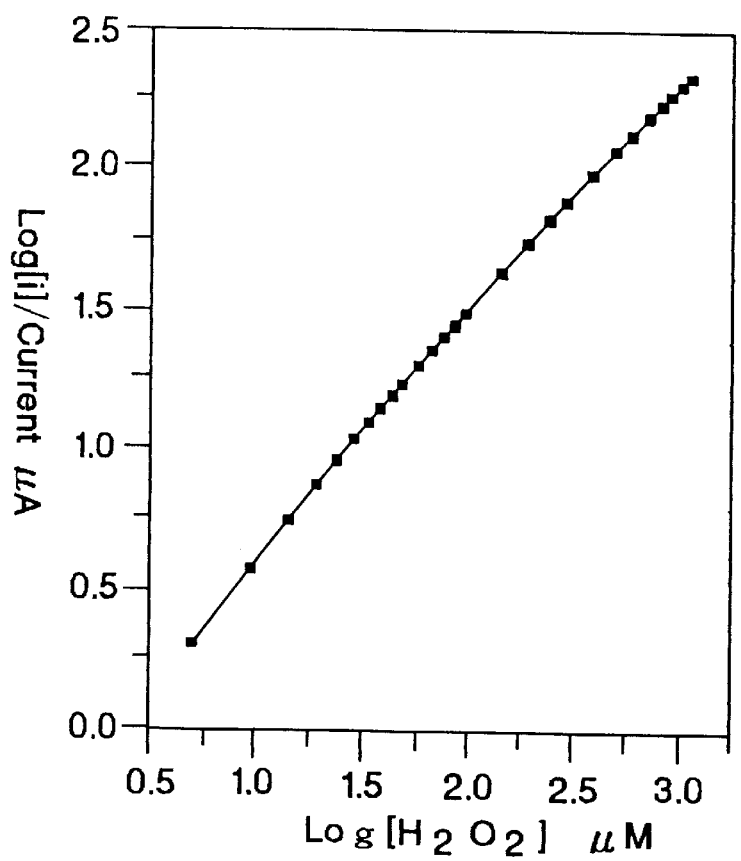
FIG. 2 is a calibration curve of the chemical sensor used in FIG. 1, wherein the concentration of $H_2O_2$ (μM) is plot versus current (μA) in a log-log manner.

At $H_2O_2$ concentration $5.0 \times 10^{-5}$ M, the response time that reached 95% of the maximum signal ($t_{95\%}$) was 6.5 seconds (not shown in the drawing). By plotting $H_2O_2$ concentration vs. current ($\mu$A), it was found that there was a linear relationship within a range from $0.5 \times 10^{-6}$ M to $2.5 \times 10^{-4}$ M (correlation coefficient=0.998). A slope of 11.8 $\mu$A/mM-mm$^2$ was obtained using least square method. If plotting $H_2O_2$ concentration vs. current ($\mu$A) in a log-log manne, the linear relationship can extend to $1.1 \times 10^{-3}$ M (correlation coefficient=0.999), as shown in FIG. 2.

The measurement was repeated for 20 times using $5.0 \times 10^{-5}$ M $H_2O_2$, and an average current 16.70 $\mu$A (ranged from 17.25 to 16.25 $\mu$A) was obtained with a relative standard deviation of 1.69%. Based on the signal-to noise characteristics (S/N)=3, it was found that the detection limit of $H_2O_2$ was $6.25 \times 10^{-8}$ M.

Further interference experiments indicated there was no substantial interference when measuring $H_2O_2$ concentration in the presence of $2.0 \times 10^{-4}$ M of ascorbic acid, uric acid, dopamine, catechol, tyrosine or acetaminophen, or $5.0 \times 10^{-5}$ M spermine and spermidine.

Example 2
$Ni_2[Fe(II)(CN)_6]$ Chemical Sensor (1). Preparation of Carbon Paste Electrode (a). $Ni_3[Fe(CN)_6]2.xH_2O$ 50 ml of 60 mM $NiCl_2$ was gradually added into a 50 ml, 40 mM $K_3[Fe(CN)_6]$ solution and kept stirring for overnight. The resulting suspension was then centrifuged and a precipitate obtained was then rinsed by deionized water several times and allowed to dry.

(b). Preparation of Carbon Paste

Carbon powder was well mixed with mineral oil with 55:45 ratio (weight) to form a pure carbon paste. Part of the pure carbon paste was mixed with the $Ni_3[Fe(CN)_6]_2$ prepared in step (a) by a weight ratio of 94:6 to form a surface carbon paste.

(c). Preparation of Electrode

Into a 56 mm long glass tube (inner diameter 3.5 mm and outer diameter 6 mm), a copper wire was inserted followed by filling with epoxy resin between the tube and copper wire except both ends of the copper wire. Moreover, the front end of the copper wire was inside the glass tube and 3 mm away from the front end of the glass tube. Then the pure carbon paste was applied to cover the front end of the copper wire and inside the glass tube, and the surface carbon paste was finally coated on the pure carbon paste.

(2). Measurement Conditions $H_2O_2$ concentration was determined by amperometry using the electrode prepared in step (b) as a working electrode at 0 V (vs. Ag/AgCl), and in 0.05 M (pH=4) acetate buffer solution, 28° C., and with constant stirring. The $Ni_3[Fe(III)(CN)_6]$ coated on the working electrode would be reduced to $Ni_2[Fe(II)(CN)_6]$ prior to or immediately at the beginning of the measurement.

Example 3
$Cr_2[Fe(II)(CN)_6]$ Chemical Sensor (1). Pretreatment of Electrode

A glassy carbon ring-disk electrode (RDE 0032, Princeton Applied Research, 6 mm outer diameter) was polished using 1 $\mu$m and 0.5 $\mu$m alumina suspensions in sequence, and sonicated for one minutes in deionized water and for another three minutes in new deionized water after each polish. The electrode surface was checked by a cyclic voltammetry (BAS 100W, Bioanalytical Systems) to ensure free of contamination.

(2). Preparation of a Glassy Carbon Ring-disk Working Electrode

The pretreated glassy carbon ring-disk electrode was immersed into a 0.1 M KCl (pH=3) electroplating solution containing 10 mM $Cr(NO_3)_3.9H_2O$ and 5 mM $K_3[Fe(III)(CN)_6]$. A cyclic voltammetry was conducted for one hour with a scan range of –0.02 to 0.95 V (vs. Ag/AgCl) at 25° C. and 400 rpm to form a thin layer on the glassy carbon ring-disk electrode. The modified glassy carbon ring-disk electrode was then conditioned in a 0.1 M KCl (pH=3) eletrolyte for 30 minutes to obtain a working electrode.

(3). Measurement Conditions $H_2O_2$ concentration was determined by amperometry using the electrode prepared in step (b) as a working electrode at 0 V (vs. Ag/AgCl), and in 0.05 M (pH=4) succinate buffer solution, 25° C., and with 900 rpm constant stirring.

Example 4
Glucose Biochemical Sensor Containing $Co_2[Fe(II)(CN)_6]$ (1). Pretreatment of Electrode A glassy carbon ring-disk electrode (RDE 0032, Princeton Applied Research, 6 mm outer diameter) was polished using 6, 3 and 1 $\mu$m diamond suspensions and 1 and 0.5 $\mu$m alumina suspensions in sequence, and sonicated for five minutes in deionized water after each polish except that ten minutes after the last polish. The electrode surface was checked by a cyclic voltammetry (BAS 100W, Bioanalytical Systems) to ensure free of contamination.

(2). Preparation of a Biochemical Working Electrode

The preparation of a biochemical working electrode was similar to the fixed-potential electroplating used in step (2) of Example 1, which comprises the following two steps:

(a) The pretreated glassy carbon ring-disk electrode, a homemade 3 M KCl Ag/AgCl reference electrode, and a platinum wire counter electrode were immersed into a 0.1 M KCl (pH=3) electroplating solution containing 15 mM $Co(NO_3)_2.6H_2O$ and 15 mM $K_3[Fe(III)(CN)_6]$. The applied potential was maintained at −50 mV (vs. Ag/AgCl) for 4 hours at 28° C. and 400 rpm to form a thin layer on the glassy carbon ring-disk electrode. The modified glassy carbon ring-disk electrode was then conditioned in a 0.1 M KCl (pH=3) eletrolyte for 10 minutes.

(b) The resulting electrode from step (a), a homemade 3 M KCl Ag/AgCl reference electrode, and a platinum wire counter electrode were immersed into a 0.1 M KCl (pH=3) electroplating solution containing 15 mM $Co(NO_3)_2 \cdot 6H_2O$, 15 mM $K_3[Fe(III)(CN)_6]$ and 25 mg glucose oxidase. The applied potential was maintained at −50 mV (vs. Ag/AgCl) for 1 hour at 28° C. and 400 rpm. The modified glassy carbon ring-disk electrode was then conditioned in a 0.05 M KCl (pH=3) eletrolyte for 10 minutes to obtain a biochemical working electrode.

(3). Measurement Conditions

Figure 3:
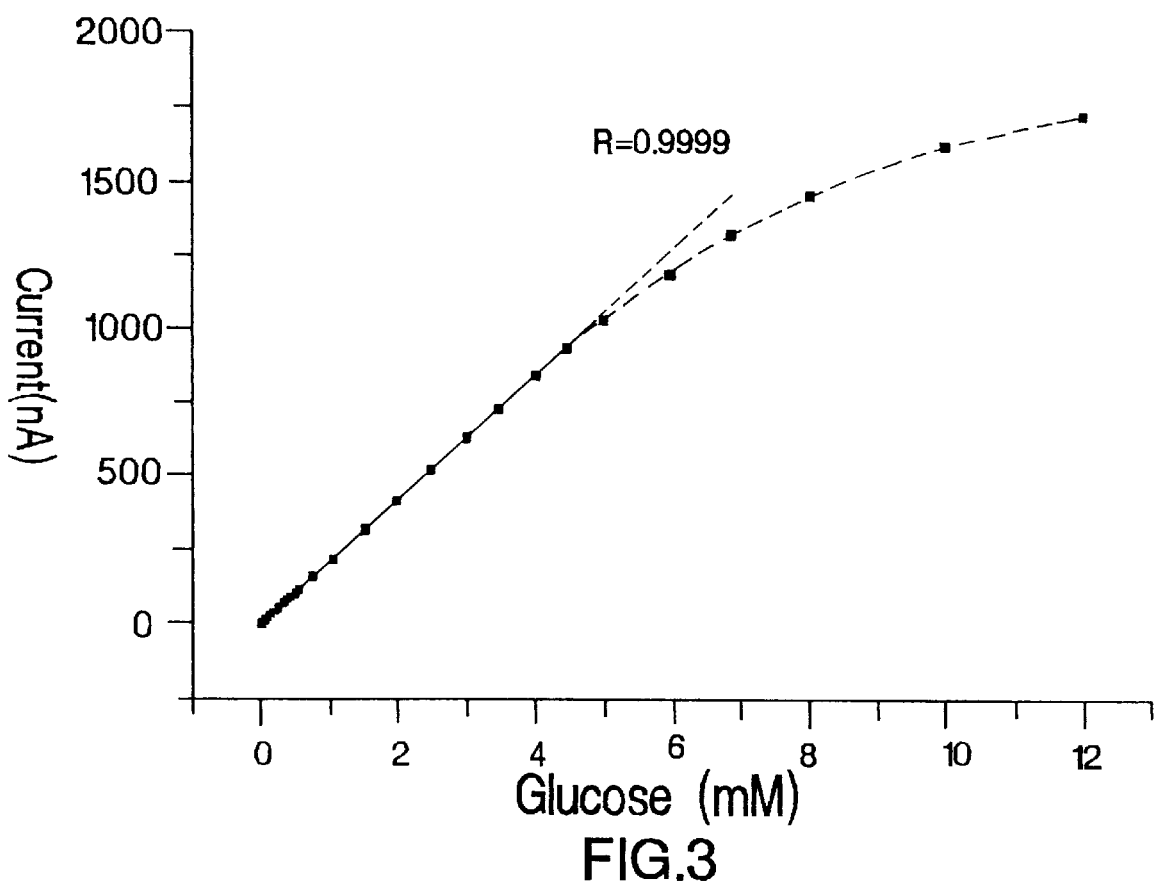
FIG. 3 is a calibration curve of a glucose biochemical sensor containing $Co_2[Fe(II)(CN)_6]$ in an amperometry analysis, wherein the y-axis is current (nA) and x-axis is the glucose concentration (mM). The glucose biochemical sensor is prepared according to another embodiment of the present invention.
Figure 3A:
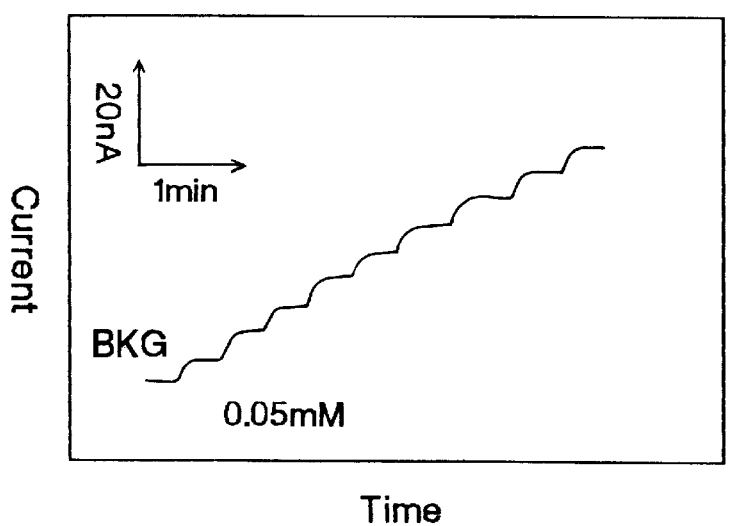
FIG. 3a shows a response of a working electrode upon ten successive injections of a glucose solution to provide an increment in glucose concentration of 0.05 mM for each addition in an amperometry analysis, where the x-axis is time, the y-axis is current (nA), and BKG represents blank background value. The working electrode is the glucose biochemical sensor used in FIG. 3.

The biochemical working electrode prepared above, a homemade 3M KCl Ag/AgCl reference electrode, and a platinum wire counter electrode were immersed in a 0.05 M phosphate buffer, pH=6 (Riedel-de Haen, RDH) with 0.05 M KCl solution in an electrochemical cell. A bi-potentiostat (model PAR, 366A, Princeton Applied Research) was used to control the applied voltage at 0 mV (vs. Ag/AgCl). The detection temperature of the electrochemical cell was kept at 28° C. with a circulator (Modle B402, Firstek Scientific). The phosphate buffer in the cell was stirred constantly at 400 rpm with a motor controlled rotor (Model 636, Princeton Applied Research). FIG. 3a shows a response of the glucose biochemical working electrode upon ten successive injections of a glucose solution to provide an increment in glucose concentration of 0.05 mM for each addition to the phosphate buffer at a constant time interval, wherein the x-axis is time, the y-axis is current (nA), and BKG represents blank background value. It can be seen from FIG. 3 that there was a linear relationship between the current and glucose consentration within a range from 0 to 5 mM (correlation coefficient=0.9999). Within the linear range of the calibration curve in FIG. 3 the electrode could monitor a very low blood sugar concentration less than 100 mg/dl. For a higher blood sugar concentration, a dilution can be performed before the measurement.

Example 5

Glucose Biochemical Sensor Containing $Ni_2[Fe(II)(CN)_6]$ (1). Preparation of Biochemical Electrode The biochemical electrode was prepared by repeating the procedures of Example 2 except that a mixture of $Ni_3[Fe(CN)_6]_2$, glucose oxidase and pure carbon paste having by a weight ratio of 6:5:89 was used to replace the surface carbon paste.

(2). Measurement Conditions

Figure 4:
FIG. 4 is a calibration curve of a glucose biochemical sensor containing $Ni_2[Fe(II)(CN)_6]$ in an amperometry analysis, wherein the y-axis is current (nA) and x-axis is the glucose concentration (mM). The glucose biochemical sensor is prepared according to a further embodiment of the present invention.
Figure 4A:
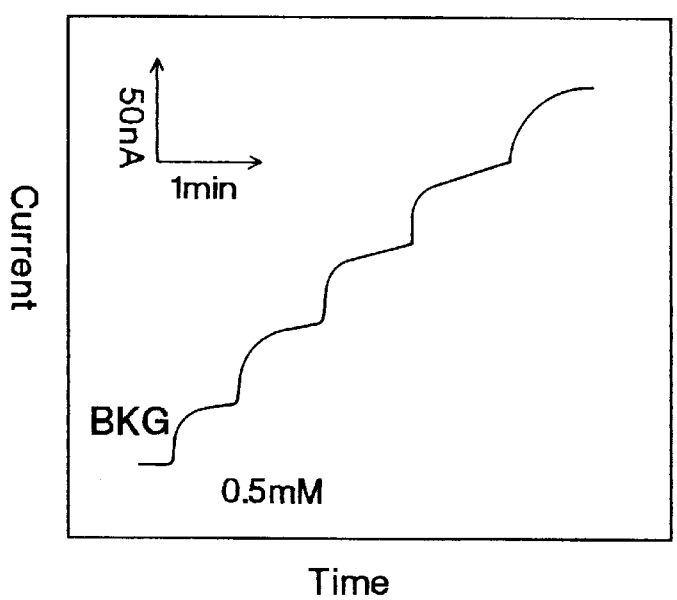
FIG. 4a shows a response of a working electrode upon ten successive injections of a glucose solution to provide an increment in glucose concentration of 0.5 mM for each addition in an amperometry analysis, where the x-axis is time, the y-axis is current (nA), and BKG represents blank background value. The working electrode is the glucose biochemical sensor used in FIG. 4.

The optimal measurement conditions were: monitoring voltage +0.02 mV (vs. Ag/AgCl), 28° C., and a constant stirring speed in a 0.05 M, pH4 acetate buffer solution. A calibration curve was established by adding a fixed amount of a glucose solution to provide an increment in glucose concentration of 0.5 mM for each addition at a constant time interval as shown in FIGS. 4a and 4. FIG. 4 indicates that there was a linear relationship between the current and glucose consentration within a range from 0 to $5.5 \times 10^{-3}$ mM (correlation coefficient=0.9999). The current density was 0.85 $\mu A/(mM \times cm^2)$, the response time for a 1 mM glucose solution was 42 seconds, and the detection limit was $1 \times 10^{-4}$ M (S/N=3). This biochemical sensor had a relative standard deviation of 3.81% when a $1 \times 10^{-3}$ M glucose solution was repeatedly measured.

Example 6

Glucose Biochemical Sensor Containing $Cr[Fe(II)(CN)_6]$ (1). Pretreatment of Electrode A glassy carbon ring-disk electrode (RDE 0032, Princeton Applied Research, 6 mm outer diameter) was polished using 0.1 $\mu m$ alumina suspension, and sonicated for three minutes in deionized water twice. The electrode surface was checked by a cyclic voltammetry (BAS 100W, Bioanalytical Systems) to ensure free of contamination. The polish and sonication were repeated until the electrode surface was free of contamination.

(2). Preparation of a Biochemical Working Electrode

The preparation of a biochemical working electrode was similar to the fixed-potential electroplating used in step (2) of Example 3, which comprises the following two steps:

(a) The pretreated glassy carbon ring-disk electrode was immersed into a 5 mL electroplating solution containing 10 mM $Cr(NO_3)_3 \cdot 9H_2O$, 5 mM $K_3[Fe(III)(CN)_6]$ and 25 mM tetrabutyl ammonium p-toluenesulfonate. A cyclic voltammetry was conducted for 0.5 hour with a scan range of −0.02 to 0.95 V (vs. Ag/AgCl) at 25° C. and 400 rpm to form a thin layer on the glassy carbon ring-disk electrode.

(b) The resulting electrode from step (a) was immersed into a 5 mL electroplating solution containing 10 mM $Cr(NO_3)_3 \cdot 9H_2O$, 5 mM $K_3[Fe(III)(CN)_6]$, 25 mM tetrabutyl ammonium p-toluenesulfonate and 2.5 mg glucose oxidase. A cyclic voltammetry was conducted for 10 minutes with a scan range of −0.02 to 0.95 V (vs. Ag/AgCl) at 25° C. and 400 rpm to obtain a biochemical working electrode.

(3). Measurement Conditions

Figure 5:
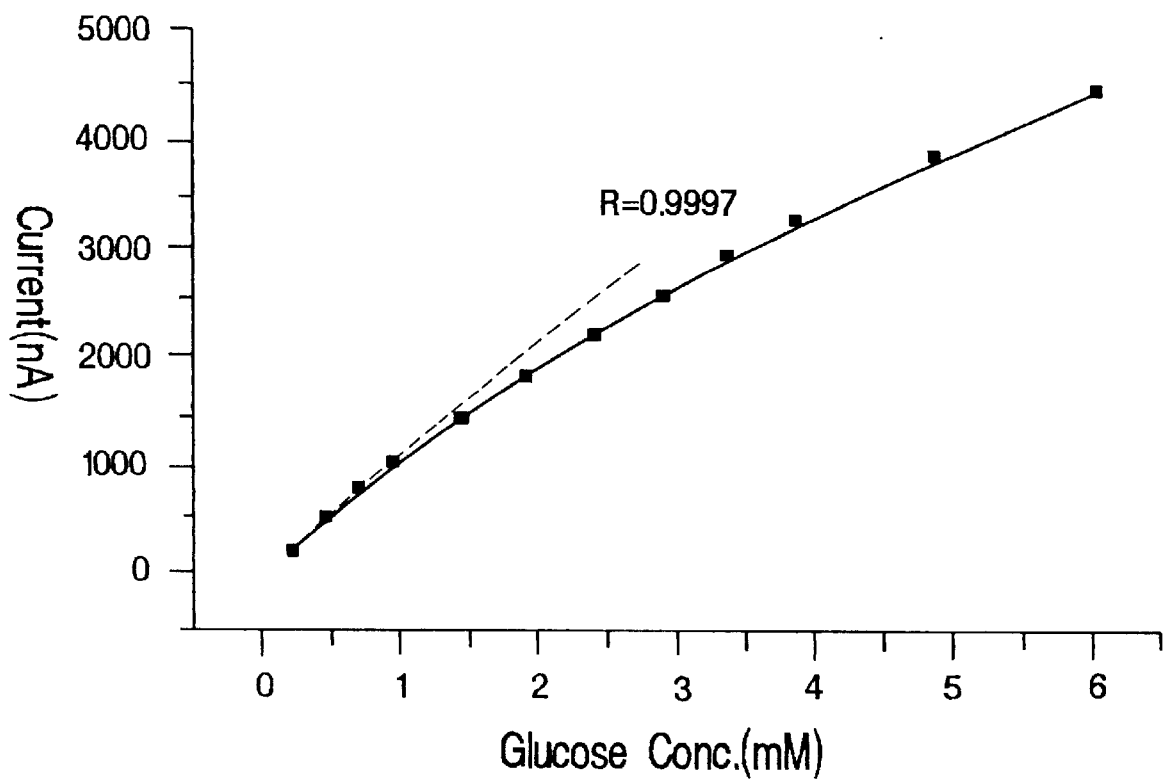
FIG. 5 is a calibration curve of a glucose biochemical sensor containing $Cr_2[Fe(II)(CN)_6]$ in an amperometry analysis, wherein the y-axis is current (nA) and x-axis is the glucose concentration ($10^{-4}$ M). The glucose biochemical sensor is prepared according to another further embodiment of the present invention.
Figure 5A:
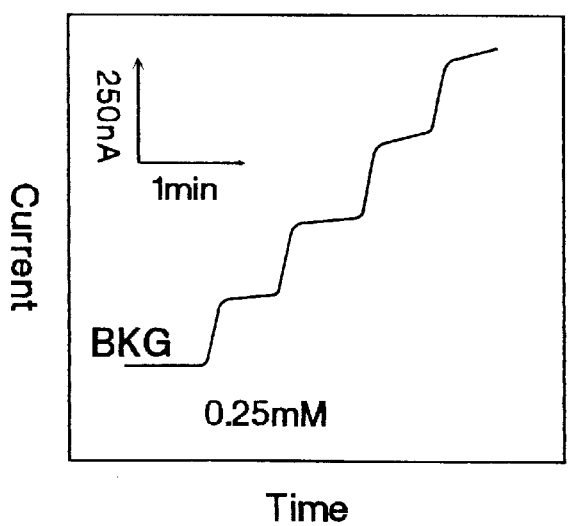
FIG. 5a shows a response of a working electrode upon ten successive injections of a glucose solution to provide an increment in glucose concentration of 0.25 mM for each addition in an amperometry analysis, where the x-axis is time, the y-axis is current (nA), and BKG represents blank background value. The working electrode is the glucose biochemical sensor used in FIG. 5.

The optimal measurement conditions were: monitoring voltage 0 V (vs. Ag/AgCl), 25° C., and a constant stirring speed in a 0.05 M, pH6 succinate buffer solution. A calibration curve was established by adding a fixed amount of a glucose solution to provide an increment in glucose concentration of 0.25 mM for each addition at a constant time interval as shown in FIG. 5a and 5. FIG. 5 indicates that there was a linear relationship between the current and glucose consentration within a range from 0 to 1 mM (correlation coefficient=0.9997).

In the Examples the working electrodes (6 mm diameter) are relatively small in size in comparison with the volume of the buffer solutions in the cell, so that a steady-state amperometric measurement is possible only when the buffer solutions are in a homogenous phase under sufficient stirring. However, a minute working electrode can be prepared by coating a small amount of the carbon paste in Examples 2 and 5 on a transducer. In this case, a small amount of solution which is able to cover the minute working electrode, the reference electrode and the counter electrode, and an instant current detected are sufficient to determine the $H_2O_2$ concentration or the $H_2O_2$ precursor concentration. When the volume of the solution is very small such that no substantial potential drop caused by the solution, the reference electrode can be omitted. Therefore, this invention also discloses a method to determine $H_2O_2$ concentration including the following steps:

a) contacting an unknown solution with an counter electrode and the $H_2O_2$ chemical sensor of the present invention at the same time;

b) conducting an amperometric measurement so that an instant current is detected from the $H_2O_2$ chemical sensor; and c) determining $H_2O_2$ concentration of the unknown solution by comparing a magnitude of the instant current obtained from step b) with a $H_2O_2$ calibration curve.

This invention further disclose a new method to determine $H_2O_2$ precursor concentration, and the procedures comprises:

a) contacting an unknown solution with an counter electrode and the $H_2O_2$ precursor chemical sensor of the present invention at the same time;

b) conducting an amperometric measurement so that an instant current is detected from the $H_2O_2$ precursor chemical sensor; and c) determining $H_2O_2$ precursor concentration of the unknown solution by comparing a magnitude of the instant current obtained from step b) with a $H_2O_2$ precursor calibration curve.

Although particular embodiments of the invention have been described, various alternations, modificatfions, and improvements will readily occur to those skilled in the art. Accordingly, the forgoing description is by way of example only and is not intended as limiting. This invention is limited only as defined in the following claims and the equivalents thereto.

What is claimed is:

1. A chemical sensor for measuring a concentration of a $H_2O_2$ precursor in a liquid, said $H_2O_2$ precursor being a compound that can produce $H_2O_2$ in said liquid under appropriate reaction conditions, which comprises a transducer which is able to conduct an electric current and a composition deposited on a surface of the transducer, wherein said composition comprises a catalyst for said $H_2O_2$ production reaction and a mixed-valence compound having a formula as follows:

$$M_y^{z+}[Fe(II)(CN)_6]$$

wherein M is Co, Ni, Cr, Sc, V, Cu, Mn, Ag, Eu, Cd, Zn, Ru, or Rh; z is the valence of M; y=4/z; and the catalyst is an urea oxidase or a cholesterol oxidase.

2. The chemical sensor according to claim 1, wherein M is Co, z=2 and y=2.

3. The chemical sensor according to claim 1, wherein M is Ni, z=2 and y=2.

4. The chemical sensor according to claim 1, wherein M is Cr, z=2 and y=2.

5. The chemical sensor according to claim 1, wherein said catalyst is urea oxidase.

6. The chemical sensor according to claim 1, wherein said catalyst is cholesterol oxidase.

7. A method for measuring $H_2O_2$ concentration in a solution comprising the following steps:

a) immersing a counter electrode, a reference electrode and a chemical sensor as a working electrode into a solution under reaction conditions;

b) obtaining a steady electric current from the working electrode by amperometry, wherein a fixed potential between the working electrode and the reference electrode is maintained, and said fixed potential ranges from 0V to –200 mV when the reference electrode is a 3 M KCl Ag/AgCl electrode; and c) comparing the steady electric current from b) with steady electric currents obtained from solutions having known $H_2O_2$ concentrations under substantially the same operating conditions and the same fixed potential used in steps a) and b);

wherein the operating conditions comprised maintaining the solution in a homogenous phase by stirring, and maintaining a substantially constant pH by adding a pH-buffer, and selectively adding an electrolyte to the measured solution, wherein the substantially constant pH is between 3 to 7;

said chemical sensor comprising a transducer which is able to conduct an electric current and a mixed-valence compound deposited on a surface of the transducer, wherein said mixed-valence compound has a formula as follows:

$$M_y^{z+}[Fe(II)(CN)_6]$$

wherein M is Co, Ni, Cr. Sc, V, Cu, Mn, Ag, Eu, Cd, Zn, Ru, or Rh; z is the valence of M; and y=4/z.

8. The method according to claim 8, wherein said pH-buffer is phosphate buffer, citrate buffer, borate buffer, perchlorate buffer or acetate buffer, and an alkali metal halide is added to the solution as said electrolyte, when M is Co, z=2 and y=2 in the formula (I).

9. The method according to claim 7, wherein said alkali metal halide is KCl.

10. The method according to claim 8, wherein said pH-buffer is phosphate buffer having a pH of about 6.

11. The method according to claim 7, wherein said pH-buffer is phosphate buffer, citrate buffer, borate buffer or acetate buffer, and no electrolyte is added to the solution, when M is Ni, z=2 and y=2 in the formula (I).

12. The method according to claim 11, wherein said pH-buffer is acetate buffer having a pH of about 4.

13. The method according to claim 7, wherein said pH-buffer is succinate buffer, phosphate buffer, acetate buffer, borate buffer, imidazole buffer, citrate buffer, ammonium chloride buffer or glycine buffer, and no electrolyte is added to the solution, when M is Cr, z=2 and y=2 in the formula (I).

14. The method according to claim 13, wherein said pH-buffer is succinate buffer having a pH of about 6.

15. The method according to claim 7, wherein the solution is kept at a constant temperature of 15–30° C.

16. A method for measuring a $H_2O_2$ precursor concentration in a solution comprising the following steps:

a) immersing a counter electrode, a reference electrode and the chemical sensor of claim 1 as a working electrode into a solution under reaction conditions;

b) obtaining a steady electric current from the working electrode by apmerometry, wherein a fixed potential between the working electrode and the reference electrode is maintained, and said fixed potential ranges from 0.0 V to –0.2 V when the reference electrode is 3 M KCl Ag/AgCl electrode; and c) comparing the steady electric current from b) with steady electric currents obtained from solutions having known concentrations of said $H_2O_2$ precursor under substantially the same operating conditions and the same fixed potential used in steps a) and b);

wherein the operating conditions comprises maintaining the solution in a homogeneous phase by stirring, and maintaining a substantially constant pH by adding a pH-buffer, and selectively adding an electrolyte to the measured solution, wherein the substantially constant pH is between 3 to 7.

17. The method according to claim 16, wherein said pH-buffer is phosphate buffer, citrate buffer, borate buffer, perchlorate buffer or acetate buffer, and an alkali metal halide is added to the solution as said electrolyte, when M is Co, z=2 and y=2 in the formula (I).

18. The method according to claim 17, wherein said alkali metal halide is KCl.

19. The method according to claim 17, wherein said pH-buffer is phosphate buffer having a pH of about 6.

20. The method according to claim 16, wherein said pH-buffer is phosphate buffer, citrate buffer, borate buffer or acetate buffer, and no electrolyte is added to the solution, when M is Ni, z=2 and y=2 in the formula (I).

21. The method according to claim 20, wherein said pH-buffer is acetate buffer having a pH of about 4.

22. The method according to claim 16, wherein said pH-buffer is succinate buffer, phosphate buffer, acetate buffer, borate buffer, imidazole buffer, citrate buffer, ammonium chloride buffer or glycine buffer, and no electrolyte is added to the solution, when M is Cr, z=2 and y=2 in the formula (I).

23. The method according to claim 22, wherein said pH-buffer is succinate buffer having a pH of about 6.

24. The method according to claim 16, wherein the solution is kept at a constant temperature of 15–30° C.

25. The chemical sensor according to claim 16, wherein M is Cr, z=2 and y=2.

26. The chemical sensor according to claim 16, wherein said catalyst is urea oxidase.

* * * * *